United States Patent [19]

Dory

[11] 4,418,698

[45] Dec. 6, 1983

[54] ULTRASONIC SCANNING PROBE WITH MECHANICAL SECTOR SCANNING MEANS

[76] Inventor: Jacques Dory, 91 rue des Molveaux, 77450 Esbly, France

[21] Appl. No.: 287,678

[22] Filed: Jul. 28, 1981

[30] Foreign Application Priority Data

Jul. 29, 1980 [FR] France ................................ 80 16717
Jul. 29, 1980 [FR] France ................................ 80 16718

[51] Int. Cl.$^3$ .............................................. A61B 10/00
[52] U.S. Cl. ....................................... 128/660; 73/633
[58] Field of Search .................. 128/660; 73/618, 620, 73/633; 358/199, 205

[56] References Cited

U.S. PATENT DOCUMENTS

| | | | |
|---|---|---|---|
| 3,955,561 | 5/1976 | Eggleton ............................. | 128/660 |
| 3,964,296 | 6/1976 | Matzuk ........................... | 128/660 X |
| 4,092,867 | 6/1978 | Matzuk ............................. | 73/633 X |
| 4,282,879 | 8/1981 | Kunii et al. ......................... | 128/660 |
| 4,325,381 | 4/1982 | Glenn ................................. | 73/620 X |

FOREIGN PATENT DOCUMENTS 2710038  7/1978  Fed. Rep. of Germany ...... 128/660

*Primary Examiner*—Kyle L. Howell
*Assistant Examiner*—Christine A. Fukushima
*Attorney, Agent, or Firm*—William A. Drucker

[57] ABSTRACT

The probe has a casing provided with an ultrasonically transmissive window and containing a couplant liquid in which are immersed a piezoelectric disc, an electric motor and a mechanical coupling between the motor shaft and the disc. The mechanical coupling comprises a connecting rod driven at one end by the shaft in a conical motion about the shaft axis, which is at right angles to the disc and to the window. The disc is rotatably supported about a diametrical axis which is fixedly positioned with respect to the casing. A yoke which has a bracket secured to the connecting rod at the opposite end thereof, is rotatably supported about an axis which is fixedly positioned with respect to the disc and at right angles to the diametrical axis. The mechanical coupling transmits an oscillating motion to the disc about the diametrical axis.

9 Claims, 10 Drawing Figures

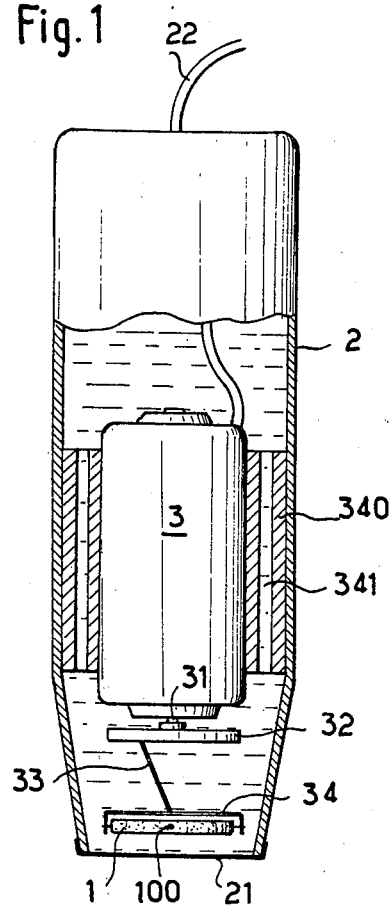
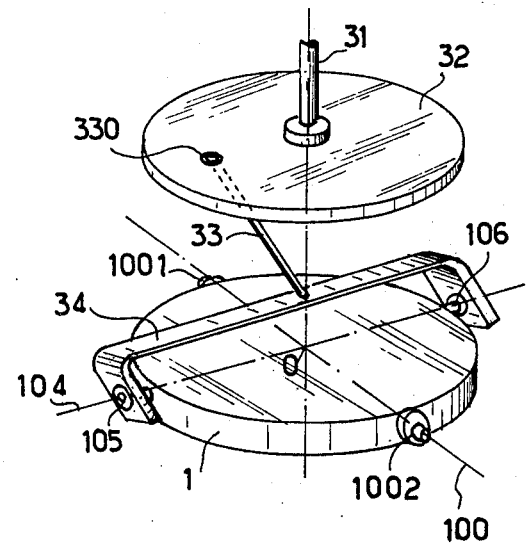
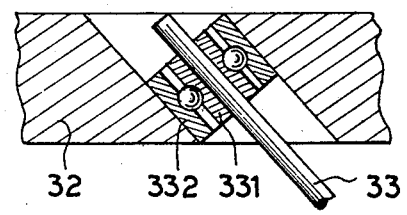
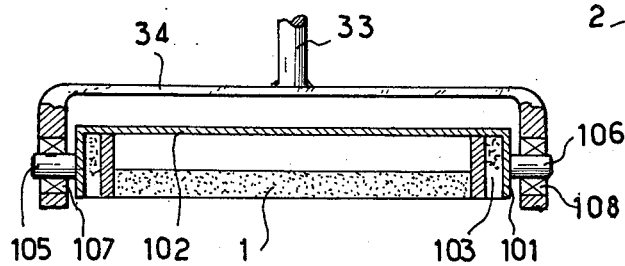
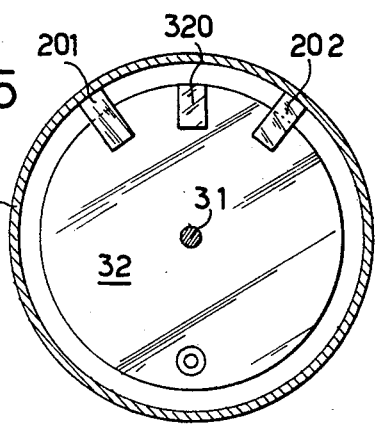

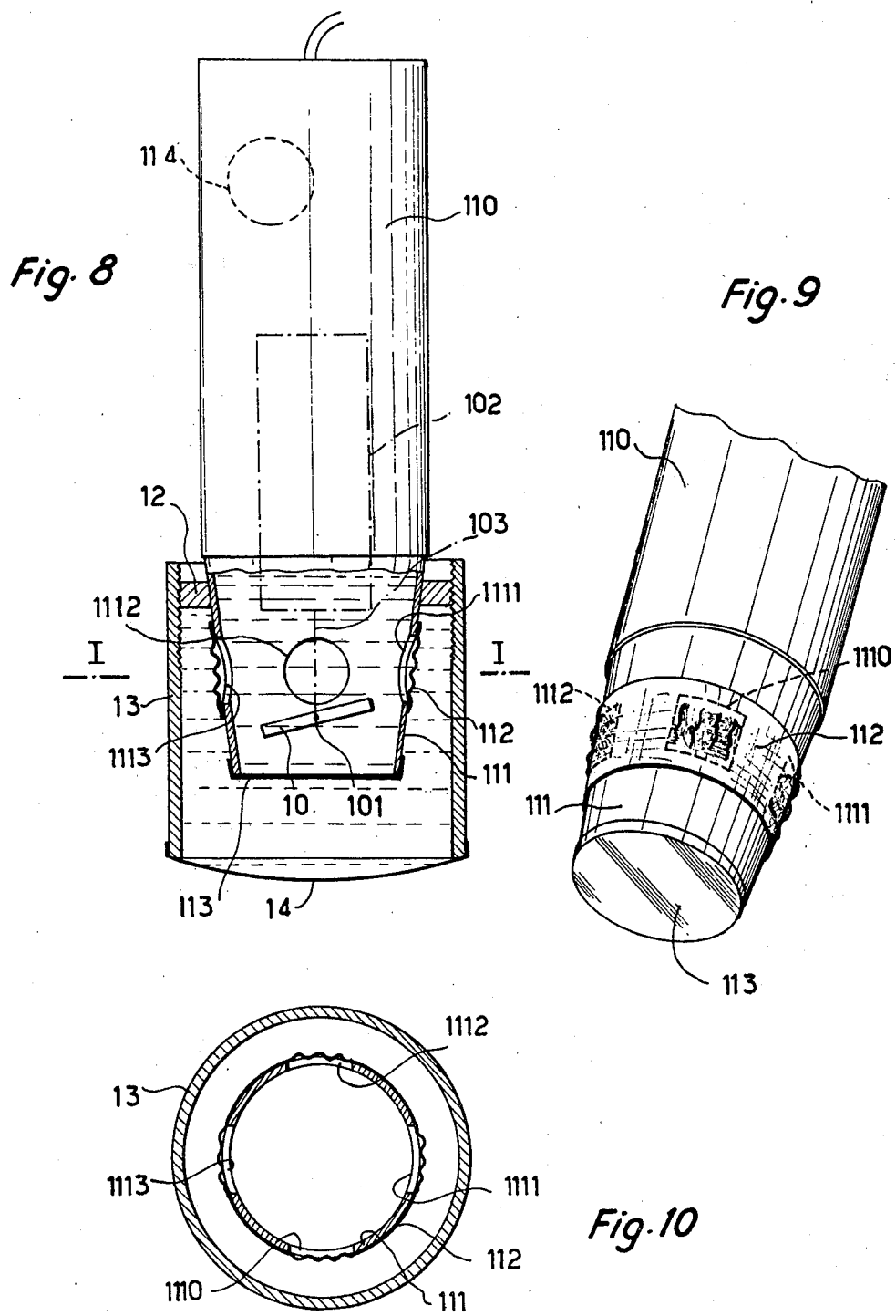

ULTRASONIC SCANNING PROBE WITH MECHANICAL SECTOR SCANNING MEANS

BACKGROUND OF THE INVENTION

The invention relates to equipment for medical ultrasonic scanning comprising an ultrasonic transducer devised to generate a beam which describes a relatively rapid angular scan in a plane of inspection and is transmitted to the medium being inspected by a couplant liquid contained in a chamber.

It relates more particularly to an ultrasonic scanning probe comprising a housing containing the couplant liquid and provided with a window through which the ultrasonic beam passes, in which are immersed a piezoelectric component in the form of a disc, an electric motor unit and mechanical means of producing the angular deviation of the beam according to the angular position of the motor shaft; the probe further preferably comprising means providing continuous indication of the angular position of the beam.

OBJECT OF THE INVENTION

Such a probe is intended for real time ultrasonic scanning in applications such as cardiology, opthalmology and obstetrics, where the number of images per second that the instrument must display is for example of the order of 25 to 50 and where it is important to have a probe that is extremely light, compact, easy to use, inexpensive and completely reliable. In some of these applications, it is useful to be able to operate the equipment either using the so called "B scan," in which the trace on the display CRT occupies, at each moment, a position representing that of the ultrasonic beam in the medium being examined, or according to the so called "TM" or "time movement" mode, in which, the probe being stationary, the changes with time of the structures being examined are displayed.

For the "B scan" mode, it is sufficient for the probe to provide a continuous indication of the angular position of the ultrasonic beam: ultrasonic scanning equipment provided with suitable facilities for controlling the deviation of the electronic beam on the basis of this information are well known, and the invention does not relate to such means.

In the "TM mode," the equipment normally comprises facilities for displaying, on the CRT screen, a bright line which can be moved on the screen to a part of the image the movement of which it is desired to observe. When this selection has been made, the ultrasonic beam should be brought into the corresponding angular position and fixed in this position and means must be provided for effecting the appropriate angular movement of the beam.

The invention provides particularly simple and advantageous mechanical means of producing the angular deviation of the ultrasonic beam.

Another of its objects is a system for indicating the angular position of the ultrasonic beam, particularly suitable for cooperating with the said means of deviation.

Finally, its object is a system which will be associated with the probe, to produce the said angular displacement of the beam suitable for changing over the inspection equipment into TM mode, a system which advantageously cooperates with the said means of deviation.

SUMMARY OF THE INVENTION

In accordance with an important special feature of the invention, the piezoelectric component being in the form of a disc, the motor unit has a shaft arranged perpendicularly to the said window along a first axis, the said mechanical means comprise a connecting rod driven in a conical motion around the said first axis, by a mechanical linkage to the said shaft so arranged that the connecting rod rotates on itself without a translational movement along its own direction, means for rotatably supporting the piezoelectric disc about a diametrical axis which is fixedly positioned with respect to the casing, the said first axis and the said diametrical axis being located in one and the same plane and perpendicular to one another and a yoke mounted for swivelling around an axis passing through the centre of the piezoelectric disc, said axis being fixedly positioned with respect to the disc and perpendicular to the said diametrical axis, the said yoke comprising a bracket fixed to that end of the said connecting rod which is not linked to the said shaft.

The invention also proposes to incorporate in a probe of the type mentioned above, in addition to a principal chamber which houses the piezoelectric disc, contains a couplant liquid in which the speed of propagation of the ultrasonic waves is appreciably different from their velocity of propagation in water, and is closed, in the direction of transmission of the ultrasonic beam, by a flexible membrane, an auxiliary chamber, bounded by the said principal membrane and by a flexible auxiliary membrane and containing water, the two membranes and the couplant liquid having substantially the same acoustic impedance as water, and at least part of the surface of the said principal membrane being sufficiently flexible to ensure equilibrium between the liquid pressures in the two chambers.

With this arrangement, the auxiliary membrane can distort when it is applied to the skin without this distortion being transmitted to the principal membrane, which forms the interface between the two liquids and, as a result, no distortion of the sound waves accompanies their refraction.

BRIEF DESCRIPTION OF THE DRAWINGS

In the attached drawings:

FIG. 1 is a schematic view, as a partial section through an axial plane, of a probe complying with a preferred mode of execution of the invention;

FIG. 2 is a schematic perspective view of the transducer drive mechanism;

FIG. 3 shows the coupling between the connecting rod and its drive member;

FIG. 4 is a detailed view of the transducer and of the yoke which causes it to oscillate.

FIG. 5 shows the magnetic device for resetting the motor into a reference position;

FIG. 8 is a sectional view of a two-membrane probe in accordance with a preferred mode of execution of the invention;

FIG. 9 is a perspective view of the end of the said probe, the outer membrane being removed and;

FIG. 10 is a section along X—X of FIG. 8.

DESCRIPTION OF THE PREFERRED EMBODIMENT

Figure 6:
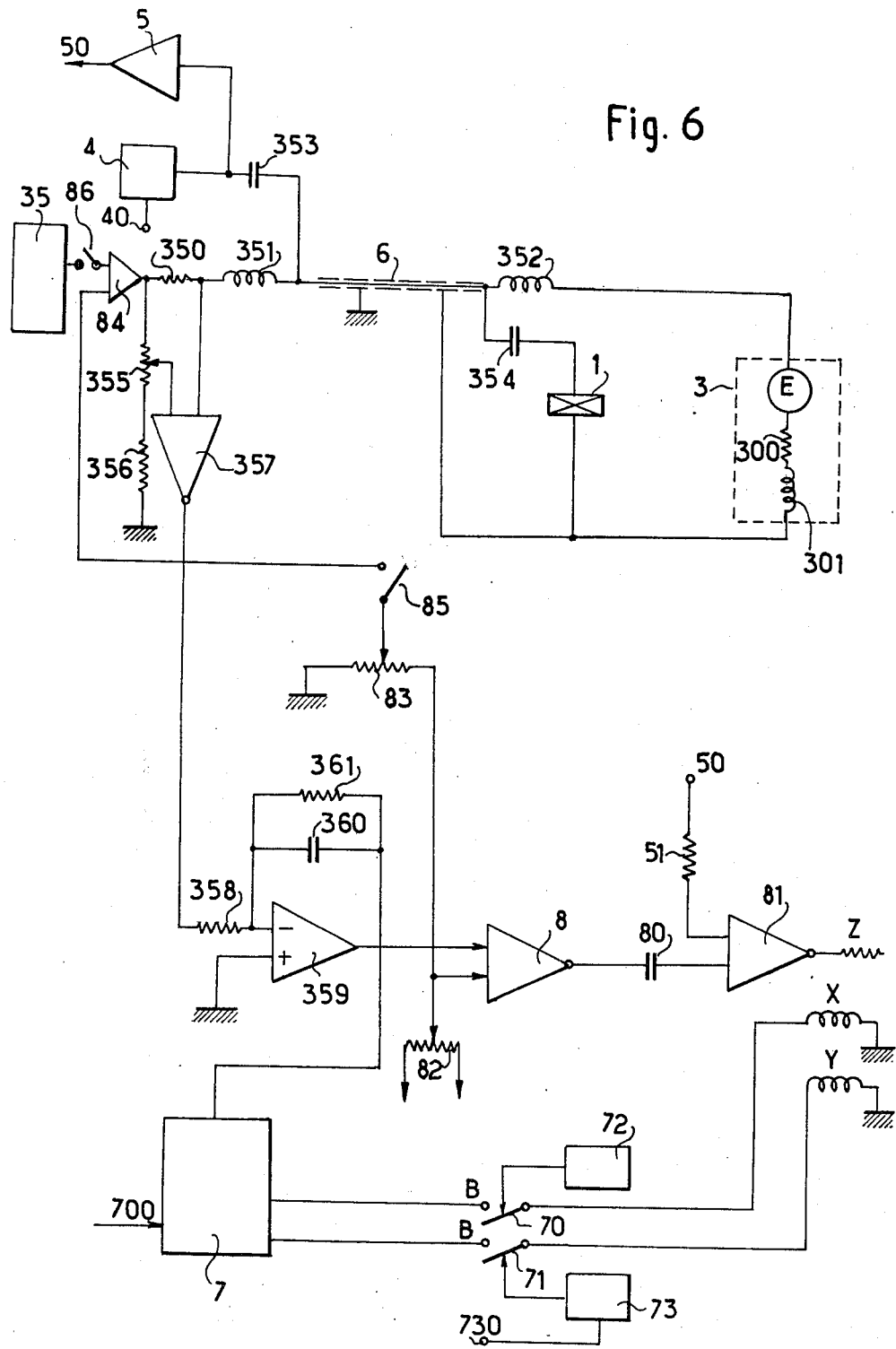
FIG. 6 is a circuit diagram of the system for indicating the angle of position of the beam and of the system which produces the angular displacement of the beam suitable for changing over into TM mode.

FIGS. 1 and 2 show a probe consisting of a piezoelectric ceramic disc-shaped pellet 1 located in proximity to a membrane 21 transparent to ultrasonic waves, in a housing 2 which contains a couplant liquid. The latter is preferably of the type in which the speed of propagation of the ultrasonic waves is lower than their speed of propagation in water, for example certain fluorinated liquids.

Such a liquid is inert, which makes it possible to use a submerged motor. The housing 2 is in the form of an elongated cylinder terminating in a frusto-conical part the end of which is closed by the membrane 21. Item 22 is a cable providing electrical connection between the probe and the transmitter and receiver circuits which the inspection equipment incorporates. The means proper to the invention which enable a single cable to be used will be explained later.

A motor 3 is fixed to the housing by means of a sleeve 340 pierced by channels 341 which allow the couplant liquid to circulate.

The transducer 1 is made to oscillate about an axis 100, perpendicular to the plane of FIG. 1, by means of a motor 3 with very low inertia, the shaft 31 of which is arranged along the axis of the housing 2 and which oscillates for example by ±20° about a reference position defined by a magnetic or elastic system, as will be explained in due course. A disc 32 is mounted on the shaft 31 perpendicular to the axis of the housing 2. A connecting rod 33 is joined to the disc 32, in a manner which will be explained in due course, at a peripheral point 330 of the disc 32; the connecting rod 33 cooperates with a yoke 34 fixed to the pellet 1, in a manner which will be explained in due course hereafter.

FIG. 3 shows the linkage between the disc 32 and the connecting rod 33. The end of the connecting rod can be seen to be fitted in bearing 331-332, in such a way that the only motion that the connecting rod 33 is able to describe with respect to the disc 32 is a rotation upon itself about its own axis, to the exclusion of any translational motion parallel to this axis.

FIG. 2 shows that the connecting rod 33 is fixed to the yoke 34 at a point such that the centreline of the said connecting rod passes through the centre 0 of the disc 1. The connecting rod therefore describes a conical motion about the axis of symmetry of the transducer, which passes through 0 and coincides with the axis of the shaft 31. The half angle of the cone will for example be of the order of 45°.

The ceramic pellet 1 is fixed to the bottom of a bush 101 which is in turn fastened to a supporting cap 102. The components 101 and 102 may be in plastic material and the gap 103 between the sidewall of the cap and the bush 101 will with advantage be filled with adhesive. On the said wall of the cap, at the two opposite ends of diameter 104 (see FIG. 2) of the pellet 1 perpendicular to the axis 100, are fitted two trunnions 105-106 (FIGS. 2 and 4) which respectively cooperate with bearings 107-108 respectively, the outer cage which is attached, as shown in FIG. 4, to the ends of the yoke 34.

It is obvious that the only motion that the disc 1 can describe is an alternating oscillation about the axis 100. The latter is defined by two trunnions 1001 and 1002 also fixed to the cap 102 and respectively cooperating with bearings, not shown, fixed to the housing 2. The axis 104 itself oscillates in the plane passing through 0 and perpendicular to axis 100, and the yoke 34 can itself only oscillate about the moving axes 104 and 33. In fact the oscillation of pellet 1, of the order of ±20° to ±25° for example, is obtained solely from rotatory motions, using components without play or slipping. It is clear that the disc 32 may be replaced by a crank.

Besides the resulting reliability, this system has the advantage that there is a unique relation between the angular positions of the shaft 31 and of the pellet 1, which facilitates the indication of the angular deviation of the transmitted beam. It will be noted that the system is completely distributed about the axis of the motor, which makes it possible to construct a coaxial probe, particularly convenient to use, notably in cardiology.

FIG. 5 shows the disc 32 seen from above and a transverse section of the housing 2. It can be seen that two small magnets 201 and 202 are fitted radially on the inner face of the housing 2, a little above the surface of the disc. The latter itself carries a radial magnet 320. These three magnets are magnetized in directions tangential to the circumference of the disc and arranged in such a way that the magnet 320 presents poles respectively opposite the poles of magnets 201 and 202, opposite poles being of the same sign. As a result, owing to repulsion, the magnet 320 will take up a position of equilibrium between the positions of magnets 201 and 202, equidistant from these if they are identical, in the absense of motor drive. The angle between the radii passing through the magnets 201 and 202 must obviously be slightly greater than the oscillatory angle of the shaft 31. In this way, a reference angular position of the shaft 31 is defined.

It will be noted that this system of magnetic damping (not shown on FIG. 2 with a view to simplification) could not only be fitted on another rotating component fastened to the motor shaft, but could be replaced by an elastic damping system using a spring or any another appropriate means. It is nevertheless particularly simple and reliable. Similarly, the motor could be replaced by a galvanometer system.

The membrane 21, in cases when the couplant liquid contained in the housing is of the type mentioned above, will with advantage be of a flexible type and associated with a second flexible membrane bounding with the first an auxiliary chamber containing water.

However in certain cases it will be possible to waive this provision and merely to line the membrane 21 with a material absorbing ultrasonic waves, with the effect of reducing spurious reflections at the membrane.

FIG. 6 shows a sawtooth of squarewave generator 35 having for example a repetition frequency of 100 Hz, intended to provide, through an amplifier 84, a resistor 350 and high value inductances 351 and 352 (for example 100 mH) linked together by a coaxial cable 6, the excitation current for the motor 3. This has been symbolized by a back-EMF (which will be proportional to speed) in series with a resistor 300 and an inductance 301.

At 4 is shown the pulse transmitter (having a repetition frequency for example of between 2 and 5 MHz) and at 5 the receiver embodied in the inspection equipment. These components are connected to the inductance 351, through a capacitor 353, while the inductance 352 is connected to the transducer 1 through a capacitor 354.

The output of the generator 35 is connected to ground through a potentiometer 355, in series with a resistor 356. A differential amplifier 357 has its output connected, through a resistor 358, to the negative input of an operational amplifier 359, the positive input of which is connected to ground. The output of amplifier 359 is connected to its negative input through a capacitor 360 on which a resistor 361 is connected in parallel. The output of the amplifier 359 is connected to the control electrode of the CRT through a circuit which will be described in due course hereafter.

The inputs of the amplifier 357 are connected to the cursor of the potentiometer 355 and, respectively, to the point common to the resistor 350 and the inductance 351.

The low frequency current which flows in the resistor 350, the inductances 351 and 352 and the rotor windings of the motor, is obviously transmitted neither to the transmitter and receiver units 4 and 5 (it is blocked by the capacitor 353), nor to the transducer 1 (capacitor 354). Similarly, the high frequency current which is transmitted by the transmitter 4 to the transducer 1 and from the latter to the receiver 5, by the capacitors 353 and 354 does not perturb (choke inductances 351–352) the path of the low frequency current mentioned above. It can be seen that in the circuit described the final result is that the connection between the transducer 1 and the external circuits can be made using a single coaxial cable.

The circuit described serves to provide, at the output of the operational amplifier 359 which functions as an integrating circuit, a voltage proportional to the angular deviation $\theta$ of the motor (and therefore of the transducer) with respect to a reference position, as will now be explained.

The series resistors 355 and 356 on the one hand, the resistor 350 is series with the motor impedance on the other hand, form a bridge in one of the diagonals of which is connected the amplifier 357. (The inductances 351 and 352 having negligible impedance at 100 Hz). When the bridge is in equilibrium, obtained when the motor is stopped by suitably adjustng the potentiometer 355, there is no potential at the terminals of the amplifier 357. In operation, the voltage at said terminals is finally proportional to the back EMF E, which it itself proportional to the speed of the motor. By integration, we therefore obtain, at the output of the amplifier 359, a voltage proportional to the angle of deviation $\theta$.

In order to obtain an absolute indication of the angular position, it is necessary first that a mechanical reference position of the oscillating assembly should be defined, and secondly that the output voltage from the integrator 359 be zero in the absence of an input signal (in order words when the motor is blocked).

The first result is obtained by means of the magnetic system already described, which brings the motor shaft into a well specified position in the absence of excitation current.

The second result is obtained by means of the capacitor 360 and the resistor 361. The capacitor 360 charges up in the presence of a voltage at the amplifier input. In the absence of such a voltage, it gradually discharges through the resistor 361, so that the amplifier output voltage is, after a certain interval, returned to zero.

The information on the angular deviation is applied to a system 7, well known in itself, which also receives at its input 700 the transmission synchronization signals (coming from terminal 40 of the transmitter 4) and provides, on the deviation electrodes X and Y of the CRT, a sawtooth potential of instantaneous amplitude proportional to $t \sin \theta$ and $t \cos \theta$ respective, where t is time. Two switches 70–71 enable these voltages to be substituted by potentials supplied by two scanning generators 72–73 respectively. The generator 72 provides a slow scan on the screen and the generator 73 a conventional type scan (a sawtooth waveform synchronized with the transmission, terminal 730 being connected to terminal 40 for this purpose).

The output of the amplifier-integrating circuit 359 is also fed to a differential amplifier 8, arranged as a comparator, the output of which is connected, through a capacitor 80, an amplifier 81 which itself is connected to the Z brightness control electrode of the CRT. The other input of the amplifier 81 is connected to the output 50 of the receiver 5 through a resistor 51, while the other input of the amplifier circuit 8 is connected to the cursor of a potentiometer 82 to the terminals of which is supplied a d-c voltage. The said cursor is connected to ground through a potentiometer 83, the cursor of which is connected to the input of amplifier 84 through a switch 85. The other input of the amplifier 84 is connected to the generator 35 through a switch 86 and its output feeds the windings of the motor 3.

When the switch 86 is closed and switch 85 open, the voltage supplied to the motor is that provided by the generator 35 and the motor describes an oscillating motion as indicated above. At this moment, the switches 70 and 71 are in the position shown as "B" on the drawing, such that the CRT tube is scanned in the B mode.

The comparator 8 compares the d-c voltage $K\theta_0$ tapped on the potentiometer 82 with the voltage $K\theta$ tapped at the output of the integrating circuit 359 and superposes on the video information fed to the Z electrode a square signal whenever $K\theta = K\theta_0$. As a result, for a given angular position of the ultrasonic beam, a bright line is displayed on the screen.

When it is desired to observe a specific structure in motion displayed on the screen according to the TM mode, the potentiometer 82 is adjusted to bring the bright line on the said structure.

At this time, the switches 70-71-85-86 are operated. The result is first that the screen is scanned, in a manner well known in itself, according to the TM mode, and secondly that the motor is no longer excited except by a d-c voltage $KK_1\theta_0$, $K_1$ being a coefficient of proportionality which depends on the setting of potentiometer 83. This voltage generates a driving torque which causes the motor rotor to turn through a certain angle, until it reaches equilibrium with the restoring torque determined by the magnetic arrangement described above. The potentiometer 83 has been set by the manufacturer so that this equilibrium position corresponds precisely to the one defined by the inlet line described above. The result is that the probe stops at the said position.

It will be appreciated that the changeover from B to TM mode is thus obtained in a simple manner, as a result of the fact that the transducer drive mechanism possesses a restoring torque to reset it into a reference position.

Figure 7:
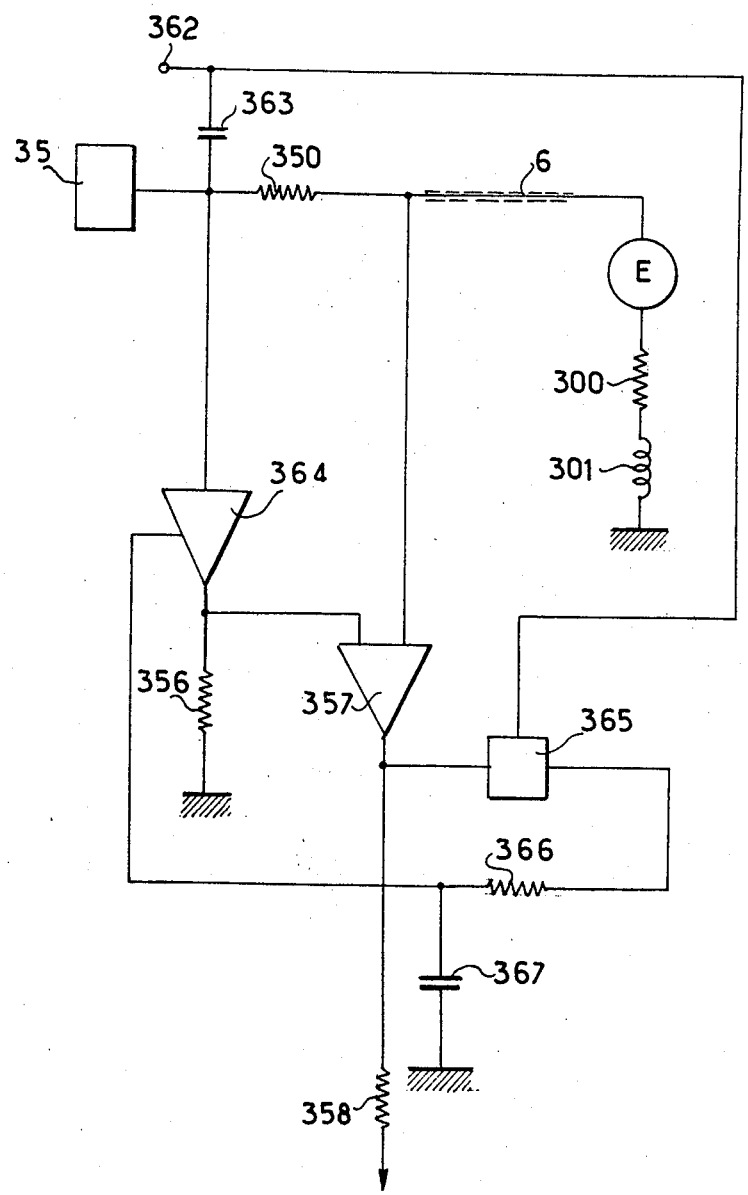
FIG. 7 shows a variant of the bridge for measuring the angular velocity of the motor, which comprises the said indication system.

FIG. 7 shows a variant of the bridge for measuring the speed of rotation of the motor which is part of the circuit of FIG. 6. In this variant the resistor 355 of FIG. 6 is replaced by a variable gain amplifier 364 in series with the resistor 356, the gain of which is controlled by a d-c voltage from a synchronous demodulator 365, after filtering through the unit made up of the resistor 366 and the capacitor 367. The synchronous demodulator 365 is fed on the one hand by the output of the differential amplifier 357 of the bridge and on the other hand by a voltage at 1000 Hz for example applied to terminal 362. This latter voltage, preferably at a high enough frequency not to drive the motor, is also fed, through a capacitor 363, to the point common to the resistor 350 and the input of the amplifier 364. The inductances 351 to 352, which play no role in the bridge balance, have not been shown in order to simplify the drawing. It is clear that at 1000 Hz, the bridge must be in balance, even if the motor is running, since it generates no back EMF at this frequency.

The demodulator 365, of a type well known in itself, generates a d-c voltage proportional in amplitude and in sign to the residual signal at 1000 Hz which is emitted from the amplifier 357 when the bridge is not balanced at 1000 Hz (for example owing to the probe being changed). This d-c voltage modifies the gain of the amplifier 364 in such a way as to restore the automatic balance of the bridge.

For purposes of simplification, FIG. 8 shows only the piezoelectric transducer 10, which describes an oscillatory motion about an axis 1010 perpendicular to the plane of the figure, driven by an electric motor, symbolized by a rectangle shown by a dotted line 1020 and a linkage mechanism, shown by a dotted line 1030. These components are housed in a metal or plastic casing, comprising a cylindrical part 110 extended by a frusto conical section 111 open at its base, joined together in a detachable manner. The frusto conical part is encircled, near its base, by a strip 112, consisting of a very thin and very flexible film, for example in natural rubber, glued to the casing, and facing this strip, the casing 111 comprises windows 1110 to 1113 (see FIGS. 9 and 10).

The base of the part 111 of the casing is closed by a membrane 113 held in position by bonding or provided with a circular lip and fitted by pressure. This membrane is made up of a relatively flexible material with an acoustic impedance water, such as a natural rubber, a silicone-containing elastomer, a polyethylene or the plastics material marketed under the name "Dutral," a trade-mark registered by the firm Montedison (polethylene-propylene).

In this latter case, the membrane is sufficiently stiff to be shaped and to keep its shape in the absence of stress, whereby, instead of being stretched flat, it can be given a predetermined curvature.

A threaded bush 12 fixed to the part 111 close to its connection with the part 110 of the casing, cooperates with a sleeve in rigid material 13 itself internally threaded at its upper end. At the base of this sleeve, a membrane 14 in flexible material having an acoustic impedance similar to that of water, for example a natural rubber, a silicone-containing elastomer or a polyurethane, is bonded or attached by peening or in any other manner.

The closed chamber bounded by the casing 110, 111, the portions of the strip 112 corresponding to the windows 1110 to 1113 and membrane 113 contains a fluorine-containing liquid the density of which is, for example, about double that of water, while the speed of propagation of ultrasonic waves therein is for example half its velocity of propagation in water; the result is that the acoustic impedance of such a liquid is virtually the same as that of water.

The closed chamber bounded by the bush 12, the sleeve 13 and the membrane 14 contains water.

The portions of the strip 112 corresponding to the windows 1110 to 1113, extremely flexible, distort in order to give a permanent pressure equilibrium between the two chambers. The result is that the distorsion of the membrane 14 when it is applied to the skin of the patient produces no deformation of the membrane 113.

In the special liquid contained in the principal chamber, one can immerse with advantage a cavity 114 filled with air closed by a flexible membrane and of which the changes in volume according to the temperature of the liquid will compensate for the pressure variation exerted by this.

The membrane 113 can be given a certain curvature and constitute for example, together with the liquid it contains, a converging lens serving to focus the ultrasonic beam. It would of course also be possible to glue a separate acoustic lens, of a type well known in itself, to the membrane 113.

It is self-evident that various modifications may be made to the arrangements described and shown, without departing from the spirit of the invention.

We claim:

1. An ultrasonic probe comprising an elongated casing containing a couplant liquid and fitted at one end with an ultrasonically transmissive window having a substantially plane surface portion, a disc-shaped piezoelectric transducer having a center and immersed in said couplant liquid, electric motor means having a shaft arranged perpendicular to said plane surface portion, mechanical means for coupling said shaft to said piezoelectric transducer, means for energizing the said motor means with an energizing signal at a first frequency whereby an oscillating motion of the shaft is obtained and resetting torque generating means for resetting the said shaft into a reference angular position when the motor means is not energized with the said first frequency, said mechanical coupling means comprising: a connecting rod having first and second ends, linkage means coupled to the first end of said connecting rod for driving the said connecting rod in a conical motion about the a first axis in which the connecting rod rotates upon itself without being allowed to effect any translation along its own length, means for rotatably supporting the said piezoelectric transducer about a diametrical axis fixedly positioned with respect to the said casing, the said first axis and the said diametrical axis being located in the same plane and perpendicular to one aother, a yoke member, means for rotatably supporting said yoke member about an axis which is fixedly positioned with respect to the transducer and passes through the center of the transducer and perpendicular to the said diametrical axis, the said yoke member having a bracket fastened to the said second end of the connecting rod.

2. A probe according to claim 1, wherein the said linkage means comprises a disc perpendicular to the said shaft and having a center which is fastened to the said shaft, a bearing in said disc at a distance from the center thereof and in which the first end of the connecting rod is rotatably supported, said resetting torque generating means comprising a first magnet, secured to the said disc and second and third magnets, secured to the said casing in positions of magnetic coupling with the first magnet such that the second and third magnets exert a restoring torque on the first magnet.

3. A probe according to claim 1, further comprising means for continuously detecting the angular position of the said shaft, said detecting means comprising bridge means connected for continuously measuring the counterelectromotive force generated by the said motor means, said bridge means providing a first output signal; means connected to the said bridge means for integrating the said first output signal, the said integrating means providing a second output signal and means, connected to the said integrating means, for cancelling out the said second output signal when said first output signal is zero.

4. A probe according to claim 3, wherein the said bridge means comprises a variable gain amplifier having a control input, the said probe further comprising a synchronous demodulator having first and second inputs and an output, means for connecting the output of the said synchronous demodulator to the control input of the variable gain amplifier, means for applying the said first output signal to the first input of the synchronous demodulator and means for applying, to the second input of the synchronous demodulator and to the said bridge means, an a-c periodic voltage having a frequency substantially higher than that of the said first frequency.

5. A probe according to claim 3, said probe further comprising means, connected to the said integrating means, for tapping a further voltage proportional to the said second output signal, means for comparing the said further voltage to an adjustable d-c reference voltage, means for generating a square wave signal when the said further voltage and reference voltage are equal, and means for applying to the motor means, a d-c voltage proportional to the said d-c reference voltage and for cancelling out the said energizing signal at a first frequency.

6. A probe according to claim 3, wherein the said window comprises a flexible membrane and the said couplant liquid is so selected that the speed of propagation of the ultrasonic waves in the said couplant liquid is substantially different from their speed of propagation in water, said probe further comprising a housing mounted about the said end of the casing and defining with the said end and the said membrane, an auxiliary chamber containing water and having a further flexible membrane, located facing the said membrane, the said membrane, the said further membrane and the said couplant liquid substantially having the same acoustic impedance as water, and the casing end having a surface portion within said auxiliary chamber which is flexible enough to ensure equilibrium of the respective liquid pressures in the casing and in the auxiliary chamber.

7. A probe according to claim 6, wherein the said surface portion of the casing comprises a flexible strip secured to a strip of rigid material provided with windows.

8. A probe according to claim 6, wherein the said housing comprises an elongated sleeve having first and second ends, said first membrane being fitted at the second end, and a displaceable means being fitted at the first end.

9. A probe according to claim 6, wherein a flexible closed container filled with air is immersed in the said couplant liquid.

* * * * *